United States Patent [19]

Beach et al.

[11] 4,349,483

[45] Sep. 14, 1982

[54] PROCESS FOR THE PREPARATION OF ALUMINUM TRIHYDROCARBYLS

[75] Inventors: David L. Beach, Gibsonia, Pa.; Adolfo Zambelli, Milan, Italy

[73] Assignee: Gulf Research & Development Company, Pittsburgh, Pa.

[21] Appl. No.: 221,063

[22] Filed: Dec. 29, 1980

[51] Int. Cl.$^3$ .............................................. C07F 5/06
[52] U.S. Cl. .................................. 260/448 A; 423/466
[58] Field of Search .................... 260/448 A; 423/466

[56] References Cited

U.S. PATENT DOCUMENTS

| | | | |
|---|---|---|---|
| 2,691,668 | 10/1954 | Ziegler et al. | 260/448 A |
| 2,744,127 | 5/1956 | Ziegler et al. | 260/448 A |
| 2,958,703 | 11/1960 | Nowlin et al. | 260/448 A |
| 3,082,232 | 3/1963 | Nowlin et al. | 260/448 A |
| 3,737,393 | 6/1973 | Vries | 252/431 R |
| 4,104,198 | 8/1978 | May, Jr. et al. | 252/429 B |
| 4,163,831 | 8/1979 | Gessell | 526/153 |

FOREIGN PATENT DOCUMENTS 2643143  6/1977  Fed. Rep. of Germany .

*Primary Examiner*—Helen M. S. Sneed
*Attorney, Agent, or Firm*—Deane E. Keith; Forrest D. Stine; Joseph J. Carducci

[57] ABSTRACT

Aluminum trihydrocarbyls are prepared by reacting an organo magnesium compound with a mixture of chlorinated and brominated aluminum compounds. There is thus obtained a mixture of aluminum trihydrocarbyls and a magnesium halide containing both chloride and bromine. The aluminum trihydrocarbyls are then recovered from the mixture. They may be used in the preparation of an alpha olfin polymerization catalyst as hereinafter described.

22 Claims, No Drawings

PROCESS FOR THE PREPARATION OF ALUMINUM TRIHYDROCARBYLS

CROSS-REFERENCES TO RELATED APPLICATIONS

Reference is made to applicants' following U.S. applications:

U.S. patent application Ser. No. 221,064, filed Dec. 29, 1980, entitled "Composition Containing Chlorine, Bromine and Magnesium."

U.S. patent application Ser. No. 221,200, filed Dec. 29, 1980, entitled "Olefin Polymerization Catalyst."

U.S. patent application Ser. No. 220,447, filed Dec. 29, 1980, entitled "Process for the Polymerization of Olefins."

FIELD OF THE INVENTION

The present invention relates to a process for preparing aluminum trihydrocarbyls by reacting an organo magnesium compound with a mixture of chlorinated and brominated aluminum compounds.

DESCRIPTION OF THE PRIOR ART

It is well known in the art to use metallic catalysts to polymerize olefins such as ethylene, propylene, 1-butene and the like to form polymers of high molecular weight. One such general class of metallic catalyst are the "Ziegler-Natta" types consisting of aluminum alkyls or alkyl halides and titanium halides. Such catalysts polymerize olefins in a stereospecific manner resulting in the formation of olefin polymers which are characterized by high degrees of isotacticity and crystallinity.

U.S. Pat. No. 4,104,198 to May, Jr., et al discloses the reaction of ethyl aluminum sesquichloride with di(n-butyl)magnesium to form a precipitate, the treatment of a slurry of this precipitate with a solution containing 480 ppm Ti and tri-n-decyl aluminum to form a catalyst, and the use of this catalyst to polymerize ethylene. U.S. Pat. No. 4,163,831 to Gessell discloses the preparation of an olefin polymerization catalyst by reacting an organomagnesium compound with a metal halide such as an aluminum trihalide to form a finely divided intermediate reaction product and thereafter mixing the intermediate reaction product with a titanium compound. German Pat. No. 2643143 to Luciani et al discloses the preparation of an olefin polymerization catalyst by reacting (a) an organometallic aluminum compound devoid of halogen atoms directly linked to the aluminum atom, (b) an electron donor compound and (c) a solid component which is the reaction product of a halogenated magnesium compound with a tetravalent titanium compound and with an electron donor compound.

SUMMARY OF THE INVENTION

It has now been found that aluminum trihydrocarbyls can be prepared by reacting an organo magnesium compound with a mixture of chlorinated and brominated aluminum compounds. There is thus obtained a mixture of aluminum trihydrocarbyls and a magnesium halide containing both chlorine and bromine. The aluminum trihydrocarbyls are then recovered from the mixture. They may be used in the preparation of an alpha olefin polymerization catalyst as hereinafter described.

The term "organo magnesium compound" is intended to include divalent hydrocarbyl magnesium compounds wherein the hydrocarbyl portion thereof can be saturated or unsaturated, straight or branched chain alkyl radicals having from about one to about 24 carbon atoms, preferably from about one to about 10 carbon atoms; aryl radicals having from about six to about 20 carbon atoms, preferably from about six to about 10 carbon atoms; alkenyl radicals having from about one to about 30 carbon atoms, preferably from about one to about 20 carbon atoms; cycloalkyl radicals having from about three to about 40 carbon atoms, preferably from about three to about 30 carbon atoms; and aralkyl and alkaryl radicals having from about six to about 40 carbon atoms, preferably from about six to about 30 carbon atoms. The organo magnesium compound can be defined by the following formula:

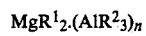

$$MgR^1{}_2 \cdot (AlR^2{}_3)_n$$

wherein n is an integer having a value of 0 or higher than 0 and preferably has a value of from 0 to 4, and each of $R^1$ and $R^2$ can be a hydrocarbyl radical as previously defined.

Specific examples of organo magnesium compounds that can be used include: diethylmagnesium, di-n-propylmagnesium, di-iso-propylmagnesium, di-n-butylmagnesium, di-sec-butylmagnesium, di-iso-butylmagnesium, di-hexylmagnesium, ethylbutylmagnesium, n-butyl-sec-butylmagnesium, diphenylmagnesium, dibenzylmagnesium, ditolylmagnesium, dicyclohexylmagnesium, magnesium aluminum pentaethyl, magnesium dialuminum octaethyl, magnesium aluminum diethyltriisobutyl, magnesium aluminum dibutyl hexaethyl, magnesium dialuminum diphenyl hexaethyl, magnesium dialuminum dibenzyl hexaethyl, magnesium dialuminum dicyclohexyl hexaethyl, magnesium dialuminum diethyl hexabutyl, etc. Of these the following organo magnesium compounds are preferred: diethylmagnesium, the dibutylmagnesiums, magnesium dialuminum octaethyl, magnesium aluminum pentaethyl, magnesium dialuminum diethyl hexa-iso-butyl and magnesium dialuminum di-iso-butyl hexaethyl.

The chlorinated and brominated aluminum compounds that can be reacted with the organo magnesium compounds defined above can be defined by the following formula:

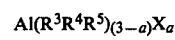

$$Al(R^3R^4R^5)_{(3-a)}X_a$$

wherein each of $R^3$, $R^4$ and $R^5$ can be a hydrocarbyl radical as defined above, X is chlorine or bromine, and a is an integer from 1 to 3. Specific examples of chlorinated and brominated aluminum compounds that can be used include: aluminum trichloride, aluminum ethyl dichloride, aluminum diethyl monochloride, aluminum isobutyl dichloride, aluminum di-isobutyl monochloride, aluminum diphenyl monochloride, aluminum dibenzyl monochloride, ethyl aluminum sesquichloride, aluminum n-butyl dichloride, aluminum di-n-butyl monochloride, aluminum sec-butyl dichloride, aluminum di-sec-butyl monochloride, aluminum propyl dichloride, aluminum dipropyl monochloride, etc. and the corresponding bromides. Of these the following chlorinated and brominated aluminum compounds are preferred: aluminum ethyl dichloride, aluminum diethyl monochloride, ethyl aluminum sesquichloride, aluminum dibutyl monochloride, aluminum butyl dichloride, etc. and the corresponding bromides, and aluminum tribromide.

DESCRIPTION OF THE PREFERRED EMBODIMENTS

In the reaction of the organo magnesium compounds with the chlorinated and brominated aluminum compounds, the molar ratios thereof can vary greatly. For example, magnesium, chlorine and bromine can be employed in the reaction mixture in the molar range of about 1.0:1.0:0.02 to about 1.0:10.0:5.0, respectively.

In carrying out the reaction it is desirable to do so in the presence of an inert liquid diluent, preferably a hydrocarbon diluent, such as benzene, toluene, cyclohexane, heptane, etc. The amount of diluent used can vary over a wide range, but generally will be such that the resultant slurry will contain from about 70 to about 99 weight percent, preferably from about 90 to about 98 weight percent, of diluent based on the total weight of the slurry.

The reaction is simply effected by stirring the slurry and maintaining the temperature thereof in the range of about $-20°$ to about $180°$ C., preferably about $25°$ to about $110°$ C., for about one minute to about 24 hours, preferably about one to about eight hours under any suitable inert atmosphere, such as nitrogen. The pressure, similarly, is not critical and ambient pressure is preferred, although pressures as low as about 25 millimeters of mercury or as high as about 100 pounds per square inch gauge (690 kPa), or even higher, can be used if desired.

The reaction mixture is then brought to ambient conditions of temperature and pressure and filtered. The recovered solids are then washed with a suitable hydrocarbon solvent, such as defined above, at ambient conditions, or in a temperature range of about $25°$ to about $100°$ C., until all the hydrocarbon-soluble constituents are removed therefrom. All of this is carried out in a suitable inert atmosphere. The aluminum trihydrocarbyls are contained in the filtrate and in the hydrocarbon washings of the solids obtained in the process. The aluminum trihydrocarbyls can be recovered in any conventional manner, for example, by subjecting the combined filtrate and hydrocarbon washings to distillation at a temperature within the range of about $50°$ to about $150°$ C. and a pressure of about 25 millimeters of mercury to about 760 millimeters of mercury to remove the solvent therefrom.

The reactions described above can be exemplified by the following representative ideal equations:

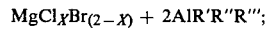

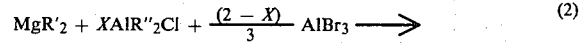

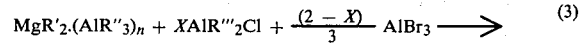

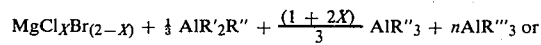

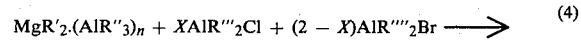

wherein each of R', R", R''', and R'''' can be a hydrocarbyl radical as previously defined, X can range from about 1.0 to about 1.98, preferably from about 1.6 to about 1.95, and most preferably from about 1.7 to about 1.95, and n is as previously defined.

An additional advantage of the present invention is that the magnesium halide solids prepared jointly with the aluminum hydrocarbyls can be recovered and used as a catalyst support for the subsequent polymerization of olefins as described hereinafter. The solids obtained in the process as previously described by filtration are dried to remove residual hydrocarbon therefrom. The solids so obtained contain substantially solely chlorine, bromine and magnesium suitable for use as a catalyst support. When used as a catalyst support, the molar ratio of bromine to chlorine should range between about 1:99 to about 50:50, preferably between about 2.5:97.5 to about 20:80, and most preferably between about 2.5:97.5 to about 15:85. The molar ratio of magnesium to combined chlorine and bromine generally should range between about 1:1.6 and about 1:2.0, preferably between about 1:1.8 and about 1:2.0. The composition will have a surface area of about 80 to about 250 square meters per gram, generally about 150 to about 200 square meters per gram.

The use of the aluminum trihydrocarbyls produced in accordance with the process of this invention in conjunction with the magnesium halide support prepared jointly therewith to prepare a polymerization catalyst will now be described. The magnesium halide support is initially treated with any suitable electron donor compound (or Lewis base). Some examples of electron donor compounds which can be used are amines, amides, ethers, ketones, nitriles, phosphines, stibenes, arsines, phosphoramides, thioethers, thioesters, aldehydes, alcoholates, amides and salts of organic acids with metals of the groups I to IV of the periodic system of elements. Suitable organic acids include aromatic acids, as for example benzoic acid or p-hydroxybenzoic acid. Some examples of typical electron donor compounds include triethylamine, N,N'-dimethylpiperazine, diethylether, n-dibutyl ether, tetrahydrofuran, acetone, acetophenone, benzonitrile, tetramethyl urea, nitrobenzene, Libutylate, dimethylaminophenyl lithium and Na-dimethylamide. Preferred electron donor compounds include esters of acids containing organic and inorganic oxygen and ethers, such as n-dibutyl ether. Some of the most suitable esters are the alkyl esters of aromatic acids, such as benzoic acid, p-methoxy- or p-ethoxybenzoic acid and p-tolyl acid, e.g., ethyl benzoate, ethyl-p-methoxybenzoate, methyl-p-toluate and ethyl-p-butoxybenzoate. Further examples of suitable esters include diethylcarbonate, triethylborate, ethylpivalate, ethylnaphthoate, ethyl-o-chlorobenzoate, ethylacetate, dimethylmaleate, alkyl- or arylsilicate and methylmethacrylate. Treatment with the electron donor compound can be accomplished, for example, by suspending the composition (magnesium-chloride bromide) in the electron donor compound, alone or in the presence of an inert liquid hydrocarbon carrier, such as defined above, so that the composition will constitute, for example, from about 10 to about 50 weight percent of the resultant slurry. The slurry can be stirred, under an inert atmosphere, as defined above, for about 10 minutes to about six hours, or even longer, preferably for about 0.5 to about four hours, at a temperature of about $25°$ to about $150°$ C., preferably about $50°$ to about $100°$ C., after which the slurry is filtered and the recovered solids are dried under a vacuum. The dried solids are then mixed with titanium tetrachloride and the mixture can be heated, for example, for about 10 minutes to about six hours, preferably for about 0.5 to about four hours, at a temperature of about 50° to about 150° C., preferably about 80° to about 140° C. The resulting mixture is then filtered, preferably while warm, and the recovered solids are then washed with a hydrocarbon solvent, such as defined above, to remove hydrocarbon soluble material therefrom. The amount of titanium tetrachloride used is that amount that will result in a recovered solid product containing from about 0.3 to about three weight percent, preferably from about 0.7 to about 2.0 weight percent of titanium, calculated as elemental titanium. All of this is done in an inert atmosphere, as before.

Prior to using the aluminum trihydrocarbyl in the polymerization catalyst, it is necessary that it be contacted with an electron donor compound, such as defined above. The molar ratio of the aluminum trihydrocarbyl to the electron donor compound can be, for example, in the range of about 0.1:1 to about 10:1, preferably about 0.5:1 to about 4:1. The treatment can be effected following the conditions outlined above in the treatment of the magnesium-chloride bromide compound with the electron donor compound. The treated aluminum trihydrocarbyl is then mixed with the solid product previously obtained, such that the molar ratio of the aluminum trihydrocarbyl to the titanium compound is in the range of about 0.1:1 to about 10:1, preferably about 0.5:1 to about 4:1. This can be accomplished by suspending the support, which has been treated with an electron donor compound and with titanium tetrachloride as previously described, in a solution containing the aluminum trihydrocarbyl and the electron donor compound.

The resulting catalyst composition can be used to polymerize alpha olefins, preferably alpha olefins having at least three carbon atoms and most preferably alpha olefins containing from three to 10 carbon atoms. Examples include propylene, 1-butene, 4-methyl-1-pentene, 1-hexene, 1-octene, 1-decene, and the like. Copolymers of such alpha olefins with each other or with ethylene can also be obtained. The alpha olefin and catalyst are contacted with each other in a polymerization reactor at a temperature of about 25° to about 150° C., preferably about 40° to about 80° C., for about one-half to about five hours, preferably for about one to about three hours using a pressure that can range from about ambient to about 1200 pounds per square inch gauge (8274 kPa), preferably in the range of about 40 to about 600 pounds per square inch gauge (276 to 4137 kPa). The catalyst is preferably in suspension in a non-reactive hydrocarbon solvent, e.g., pentane, hexane, heptane, cyclopentane, cyclohexane, benzene, toluene, xylene, etc.

At the end of the polymerization period, the pressure is released, and the reaction product is filtered, washed with a solvent, such as isopropanol, and the solid polymers are recovered and then dried. The isotacticity of polymers resulting from the polymerization process defined above will be in excess of about 90 percent and will generally be in the range of about 97 to about 99 percent. The polymer yield using the defined catalyst will be in excess of about 55,000 grams per gram of titanium in the catalyst, generally will be in the range of about 65,000 to about 200,000, or even higher, grams of polymer per gram of titanium. The polymer particle diameter will be such that substantially all (above 99 percent) will have a particle diameter in excess of 90 microns. This means they can easily be handled and will be less susceptible to atmospheric oxidation.

The following example illustrates the invention, and is not intended to limit the invention, but rather, is presented for purposes of illustration.

EXAMPLE

Into a 250 milliliter, three-necked round bottom flask equipped with a reflux condenser, a 50 milliliter addition funnel and a magnetic stirring bar was added 5.2 grams of $MgAl_2(C_2H_5)_6(C_4H_9)_2$, obtained from 25.2 milliliters of a 0.6 molar solution of $Mg(C_4H_9)_2$, in heptane/hexane. To the addition funnel was added, under dry nitrogen, 0.24 grams of $AlBr_3$ and 13.8 milliliters of a 25 weight percent solution in heptane of diethylaluminum chloride. The addition funnel was gently heated to dissolve the $AlBr_2$ and the resultant solution was added rapidly to the flask. The flask was heated to reflux and maintained at reflux, with stirring in a hot oil bath under dry nitrogen, for six hours. The resultant mixture was cooled and filtered in vacuuo yielding 1.6 grams of magnesium halide. The filtrate, containing heptane and trialkylaluminum compounds was fractionally distilled, yielding 5.8 grams of trialkylaluminum comprising a mixture of compounds having the formulas $Al(C_2H_5)_3$, $Al(C_2H_5)_2(C_4H_9)$, $Al(C_2H_5)(C_4H_9)_2$ and $Al(C_4H_9)_3$.

Although the invention has been described in considerable detail with particular reference to certain preferred embodiments thereof, variations and modifications can be effected within the spirit and scope of the invention as described hereinbefore, and as defined in the appended claims.

We claim:

1. A process for preparing aluminum trihydrocarbyls which comprises reacting an organo magnesium compound with a mixture of chlorinated and brominated aluminum compounds to obtain a magnesium halide containing both chlorine and bromine and aluminum trihydrocarbyls and then recovering said aluminum trihydrocarbyls.

2. A process as defined in claim 1 wherein the molar ratios of magnesium to chlorine to bromine compounds which are combined ranges between about 1.0:1.0:0.2 to about 1.0:10.0:5.0.

3. A process as defined in claim 1 wherein said organo magnesium compound is a divalent hydrocarbyl magnesium compound wherein the hydrocarbyl portion thereof is a radical selected from the group consisting of alkyl radicals having from about one to about 24 carbon atoms, aryl radicals having from about six to about 20 carbon atoms, alkenyl radicals having from about one to about 30 carbon atoms, cycloalkyl radicals having from about three to about 40 carbon atoms, and aralkyl and alkaryl radicals having from about six to about 40 carbon atoms.

4. A process as defined in claim 3 wherein said organo magnesium compound is selected from the group consisting of diethylmagnesium, di-n-propylmagnesium, di-iso-propylmagnesium, di-n-butylmagnesium, di-sec-butylmagnesium, di-iso-butylmagnesium, di-hexylmagnesium, ethylbutylmagnesium, n-butyl-sec-butylmagnesium, diphenylmagnesium, dibenzylmagnesium, ditolylmagnesium, dicyclohexylmagnesium, magnesium aluminum pentaethyl, magnesium dialuminum octaethyl, magnesium aluminum diethyltriisobutyl, magnesium aluminum dibutyl hexaethyl, magnesium dialuminum diphenyl hexaethyl, magnesium dialuminum dibenzyl hexaethyl, magnesium dialuminum dicyclohexyl hexaethyl and magnesium dialuminum diethyl hexabutyl.

5. A process as defined in claim 1 wherein said chlorinated and brominated aluminum compounds have the formula:

$$Al(R^3R^4R^5)_{(3-a)}X_a,$$

wherein each of $R^3$, $R^4$, and $R^5$ is a hydrocarbyl radical selected from the group consisting of alkyl radicals having from about one to about 24 carbon atoms, aryl radicals having from about six to about 20 carbon atoms, alkenyl radicals having from about one to about 30 carbon atoms, cycloalkyl radicals having from about three to about 40 carbon atoms, and aralkyl and alkaryl radicals having from about six to about 40 carbon atoms, X is chlorine or bromine and a is an integer from 1 to 3.

6. A process as defined in claim 5 wherein said chlorinated and brominated aluminum compounds are selected from the group consisting of aluminum trichloride, aluminum ethyl dichloride, aluminum diethyl monochloride, aluminum isobutyl dichloride, aluminum di-isobutyl monochloride, aluminum diphenyl monochloride, aluminum dibenzyl monochloride, ethyl aluminum sesquichloride, aluminum n-butyl dichloride, aluminum di-n-butyl monochloride, aluminum sec-butyl dichloride, aluminum di-sec-butyl monochloride, aluminum propyl dichloride, aluminum dipropyl monochloride, and the corresponding bromides.

7. A process as defined in claim 1 wherein said compounds are combined in an inert diluent to form a slurry.

8. A process as defined in claim 2 wherein said compounds are combined in an inert diluent to form a slurry.

9. A process as defined in claim 4 wherein said compounds are combined in an inert diluent to form a slurry.

10. A process as defined in claim 6 wherein said compounds are combined in an inert diluent to form a slurry.

11. A process as defined in claim 7 wherein said slurry is maintained at a temperature in the range of about $-20°$ C. to about 180° C. for about one minute to about 24 hours.

12. A process as defined in claim 7 wherein said slurry is maintained at a temperature in the range of about 25° to about 110° C. for about one to about eight hours.

13. A process as defined in claim 8 wherein said slurry is maintained at a temperature in the range of about $-20°$ C. to about 180° C. for about one minute to about 24 hours.

14. A process as defined in claim 8 wherein said slurry is maintained at a temperature in the range of about 25° to about 110° C. for about one to about eight hours.

15. A process as defined in claim 9 wherein said slurry is maintained at a temperature in the range of about $-20°$ C. to about 180° C. for about one minute to about 24 hours.

16. A process as defined in claim 9 wherein said slurry is maintained at a temperature in the range of about 25° to about 110° C. for about one to about eight hours.

17. A process as defined in claim 10 wherein said slurry is maintained at a temperature in the range of about $-20°$ C. to about 180° C. for about one minute to about 24 hours.

18. A process as defined in claim 10 wherein said slurry is maintained at a temperature in the range of about 25° to about 110° C. for about one to about eight hours.

19. A process as defined in claim 7 wherein following said reaction, the slurry is filtered and the filtrate is subjected to distillation at a temperature within the range of about 50° to about 150° C. and a pressure of about 25 millimeters of mercury to about 760 millimeters of mercury to remove solvent therefrom.

20. A process as defined in claim 8 wherein following said reaction, the slurry is filtered and the filtrate is subjected to distillation at a temperature within the range of about 50° to about 150° C. and a pressure of about 25 millimeters of mercury to about 760 millimeters of mercury to remove solvent therefrom.

21. A process as defined in claim 9 wherein following said reaction, the slurry is filtered and the filtrate is subjected to distillation at a temperature within the range of about 50° to about 150° C. and a pressure of about 25 millimeters of mercury to about 760 millimeters of mercury to remove solvent therefrom.

22. A process as defined in claim 10 wherein following said reaction, the slurry is filtered and the filtrate is subjected to distillation at a temperature within the range of about 50° to about 150° C. and a pressure of about 25 millimeters of mercury to about 760 millimeters of mercury to remove solvent therefrom.

* * * * *